US00PP26438P2

(12) United States Plant Patent
Verlinden

(10) Patent No.: US PP26,438 P2
(45) Date of Patent: Mar. 1, 2016

(54) ***VERBENA* PLANT NAMED 'VEAZ0019'**

(50) Latin Name: *Verbena hybrida*
Varietal Denomination: VEAZ0019

(71) Applicant: SYNGENTA PARTICIPATIONS AG, Basel (CH)

(72) Inventor: Kathryn Verlinden, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 144 days.

(21) Appl. No.: 14/120,144

(22) Filed: Apr. 29, 2014

(51) Int. Cl.
*A01H 5/02* (2006.01)

(52) U.S. Cl.
USPC ..... Plt./308

(58) Field of Classification Search
USPC ..... Plt./308
See application file for complete search history.

(56) References Cited

PUBLICATIONS

UPOV hit for *Verbena* plant named 'VEAZ0019', QZ PBR 39724, granted Apr. 15, 2015.*

* cited by examiner

*Primary Examiner* — Anne Grunberg
(74) *Attorney, Agent, or Firm* — Joshua L. Price

(57) ABSTRACT

A new *Verbena* plant named 'VEAZ0019' particularly distinguished by the large, purple-violet and white bi-colored inflorescences, deep green foliage, and an outwardly spreading plant habit.

1 Drawing Sheet

Latin name of the genus and species of the plant claimed: *Verbena hybrida.*

Varietal denomination: 'VEAZ0019'.

BACKGROUND OF THE NEW PLANT

The present invention comprises a new *Verbena*, botanically known as *Verbena hybrida*, and hereinafter referred to by the variety name 'VEAZ0019'.

'VEAZ0019' is a product of a planned breeding program. The new cultivar has bi-colored, purple-violet and white, large inflorescences, deep green foliage, and an outwardly spreading plant habit.

'VEAZ0019' originated from a hybridization made in August 2010 in a greenhouse in Enkhuizen, The Netherlands.

The female parent was an unpatented proprietary plant designated 'M0128-1' with purple blue and white flower color and a compact, trailing plant habit.

The male parent of 'VEAZ0019' was the proprietary plant designated '2153-2', having a purple-violet flower color and an upright, freely branching plant habit The seed was sown in February 2011 in a greenhouse in Enkhuizen, The Netherlands. 'VEAZ0019' was selected as one flowering plant within the progeny of the stated cross in August 2011.

The first act of asexual reproduction of 'VEAZ0019' was accomplished when vegetative cuttings were propagated from the initial selection in August 2011 in a greenhouse in Enkhuizen, The Netherlands.

BRIEF SUMMARY OF INVENTION

Horticultural examination of plants grown from cuttings of the plant initiated in August 2011, and continuing thereafter, has demonstrated that the combination of characteristics as herein disclosed for 'VEAZ0019' are firmly fixed and are retained through successive generations of asexual reproduction.

'VEAZ0019' has not been observed under all possible environmental conditions. The phenotype may vary significantly with variations in environment such as temperature, light intensity, and day length.

A Plant Breeder's Right for this cultivar was applied for in the Community Plant Variety Office on May 3, 2013 (2013/1232). 'VEAZ0019' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0019' with colors being as true as possible with an illustration of this type.

Figure 1:
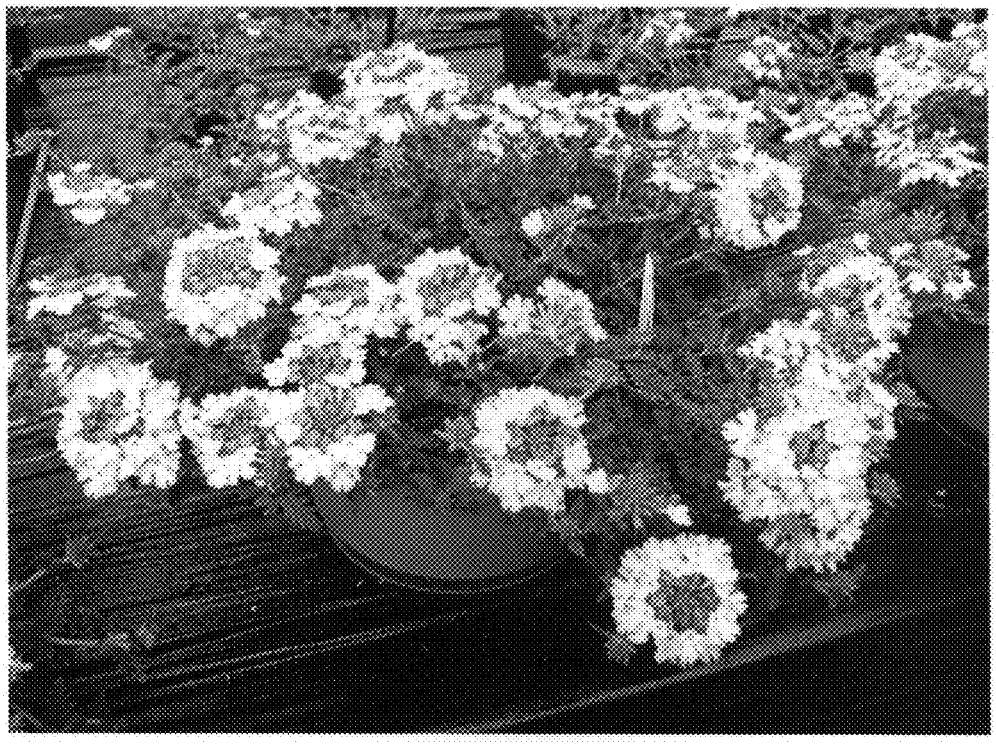
Figure 2:
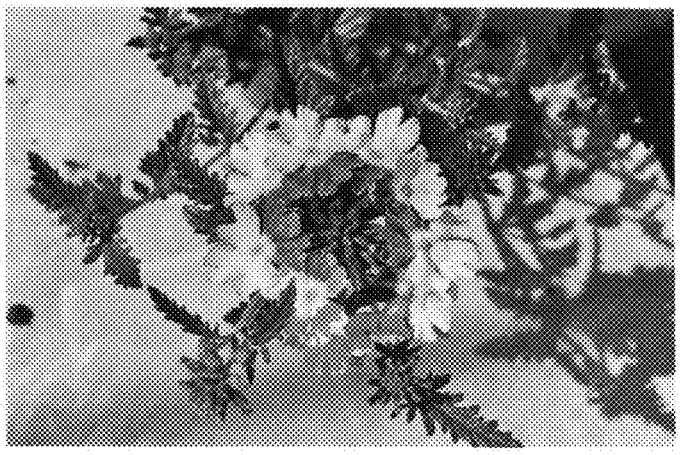

The photographic drawing in FIG. 1 shows three flowering plants of the new variety in a hanging basket and in FIG. 2 a close-up of the inflorescence.

DETAILED BOTANICAL DESCRIPTION

The plant descriptions and measurements were taken in Andijk, The Netherlands on Apr. 7, 2014 indoors in natural light. The plants used were about 10 weeks of age, growing in a 25 cm hanging basket, three plants each, in a greenhouse.

The aforementioned photographs were taken on the same day showing the same three plants in a hanging basket in a greenhouse in Andijk, The Netherlands, as described.

Color references are made to The Royal Horticultural Society Colour Chart (R.H.S.) 2001.

TABLE 1

DIFFERENCES BETWEEN THE NEW VARIETY 'VEAZ0019' AND A MOST SIMILAR VARIETY

| | 'VEAZ0019' | 'VEAZ0012' (U.S. Plant Pat. No. 23,659) |
|---|---|---|
| Inflorescence, shape: | Larger, almost flat | Smaller, more rounded ('dome'-shaped) |
| Flower colors: | Purple-violet and white | Purple and lilac and white |
| Leaf, size: | Larger | smaller |

Plant:

*Form, growth and habit.*—Herbaceous, initially semi-upright, then outwardly spreading; vigorous and free-branching.

*Plant height.*—13.0 cm.

*Plant height* (*inflorescence included*).—28.0 cm.

*Plant width.*—39.0 cm.

Roots:

*Number of days to initiate and produce roots.*—10-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 147A.

*Immature, leaf color, lower surface.*—RHS 137B.

*Mature, leaf color, upper surface.*—RHS 137A.

*Mature, leaf color, lower surface.*—RHS 137B.

*Length.*—3.5 cm.

*Width.*—2.6 cm.

*Shape.*—Ovate.

*Base shape.*—Cordate.

*Apex shape.*—Acute.

*Margin.*—Divided, sinuate.

*Texture, upper surface.*—Densely pubescent.

*Lower surface.*—Canescent; glandular hairs.

*Color of veins, upper surface.*—RHS 144B.

*Color of veins, lower surface.*—RHS 147C.

*Pattern of veining.*—Pinnate.

*Petiole, color.*—RHS 147B.

*Petiole, length.*—0.5 cm.

*Petiole, width.*—0.15 cm.

*Texture.*—Hirsute; glandular hairs.

Stem:

*Branching characteristics.*—Potentially at every node.

*Quantity of main branches per plant.*—About 5.

*Color of stem.*—RHS 143C.

*Stem length.*—12-16 cm.

*Stem width.*—0.3 cm.

*Length of internodes.*—Approximately 2-4 cm.

*Texture.*—Canescent.

*Color of peduncle.*—RHS 144B.

*Length of peduncle.*—4.5-6.5 cm.

*Peduncle diameter.*—0.2 cm.

*Texture.*—Canescent.

Inflorescence:

*Type.*—Umbel-like, but actually a spike, umbrella-shaped to nearly semi-spherical.

*Blooming habit.*—Continuously flowering through the summer months.

*Lastingness of individual blooms on the plant.*—About 4 days in the greenhouse.

*Fragrance.*—Very slight.

*Number of inflorescences per plant.*—About 35 at various stages.

*Horizontal diameter of inflorescence.*—About 6 cm.

*Depth of inflorescence.*—4 cm.

*Number of florets per inflorescence* (*including any buds at the time*).—28.

Bud (just when opening/showing color):

*Color.*—RHS 79D, purple, with RHS 149C.

*Length.*—0.4 cm.

*Width.*—0.3 cm.

*Shape.*—Tubular with bulbous apex.

Floret:

*Form.*—Sessile; salver-shape, composed of 5 partly fused petals with a base of a narrow tube.

*Immature color,* 2 *top petals, upper surface.*—N81A with N80B shades, and a small white ring around the center.

*Immature color,* 2 *top petals, lower surface.*—RHS N80D.

*Immature color,* 3 *lower petals, upper surface.*—From RHS 150C, near center, to N82C near margins.

*Immature color,* 3 *lower petals, lower surface.*—White, RHS 157D.

*Mature color,* 2 *top petals, upper surface.*—N81B with N80B shades, and a small white ring around the center.

*Mature color,* 2 *top petals, lower surface.*—RHS N80D.

*Mature color,* 3 *lower petals, upper surface.*—From RHS 150C, near center, to N82C purple-violet, near margins.

*Mature color,* 3 *lower petals, lower surface.*—White, RHS 155A.

*Floret diameter.*—2.3 cm.

*Floret length* (*depth*).—2.5 cm.

*Petal length.*—1.0 cm.

*Petal width.*—1.1 cm.

*Shape.*—Ob-cordate.

*Apex shape.*—Emarginate.

*Margin.*—Entire.

*Petal texture, upper surface.*—Papillose; very few glandular hairs.

*Petal texture, lower surface.*—Glabrous.

*Corolla tube length.*—1.6 cm.

*Corolla tube width.*—0.15 cm.

*Corolla tube color inside.*—RHS 150D.

*Tube color outside.*—RHS 150D to RHS 145D at floret base.

*Corolla texture, inside.*—Papillose, long white hairs and short hair.

*Corolla texture, outside.*—Glabrous.

*Throat hair color.*—RHS 155D but whiter.

Calyx:

*Type.*—Five sepals whose margins are fused to each other along their length, with a transparent membrane of less than 0.1 cm in width, and with one smaller sepal attached to the base of the calyx.

*Color of sepals.*—RHS 143B.

*Length of sepals.*—1.3 cm.

*Width of sepals.*—0.2 cm.

*Sepal shape.*—Fused, linear.

*Apex shape.*—Acute.

*Margins.*—Entire.

*Texture.*—Densely covered with short hair, also glandular hairs.

Reproductive organs:

*Gynoecium*.—Pistil: 1. Pistil length: 1.5 cm. Style color: RHS N144D. Style length: 1.4 cm. Stigma color: RHS 144A. Ovary color: RHS 144B. Ovary length: 0.2 cm. Ovary width: 0.1 cm.

*Androecium*.—Stamens: Anthers and filaments fused to upper half of corolla tube; four anthers with two pollen sacs per anther. Color of filaments: RHS 151D. Filament length: 0.1 cm. Anther color: RHS 151D. Anther length: 0.1 cm. Pollen amount: Little. Pollen color RHS 1B.

Fertility/seed set: No seed set observed to date.

Disease/pest resistance: Has not been determined to date.

What is claimed is:

1. A new and distinct variety of *Verbena* plant named 'VEAZ0019' substantially as illustrated and described herein.

* * * * *